US010506925B2

(12) United States Patent
Huter et al.

(10) Patent No.: US 10,506,925 B2
(45) Date of Patent: Dec. 17, 2019

(54) REFLECTOMETRY INSTRUMENT AND METHOD FOR MEASURING MACULAR PIGMENT

(71) Applicant: ZeaVision, LLC, Chesterfield, MO (US)

(72) Inventors: Scott J. Huter, Temecula, CA (US); Kevin Martin Magrini, Temecula, CA (US); Edward Allen DeHoog, Long Beach, CA (US); Jeff Alan Burke, Temecula, CA (US); Nathan Franklin Engel, Murrieta, CA (US)

(73) Assignee: ZeaVision, LLC, Chesterfield, MO (US)

( * ) Notice: Subject to any disclaimer, the term of this patent is extended or adjusted under 35 U.S.C. 154(b) by 29 days.

(21) Appl. No.: 15/887,639

(22) Filed: Feb. 2, 2018

(65) Prior Publication Data

US 2018/0242843 A1     Aug. 30, 2018

Related U.S. Application Data

(60) Provisional application No. 62/464,028, filed on Feb. 27, 2017.

(51) Int. Cl.
*A61B 3/12* (2006.01)
*G01J 3/42* (2006.01)
(Continued)

(52) U.S. Cl.
CPC .............. *A61B 3/12* (2013.01); *A61B 3/0025* (2013.01); *A61B 3/10* (2013.01); *A61B 3/145* (2013.01);
(Continued)

(58) Field of Classification Search
CPC ........... A61B 3/152; A61B 3/14; A61B 3/102; A61B 3/12; A61B 3/0025
(Continued)

(56) References Cited

U.S. PATENT DOCUMENTS

| 4,861,154 A | 8/1989 | Sherwin |
| 4,889,422 A | 12/1989 | Pavlidis |

(Continued)

FOREIGN PATENT DOCUMENTS

| EP | 0 215 566 A2 | 3/1987 |
| GB | 1 012 838 A | 12/1965 |
| WO | WO 2012-051449 A1 | 4/2012 |

OTHER PUBLICATIONS

"Fast and Objective Measurement of Macular Pigment With Natural Pupil" (Dirk van Norren, Jan van de Kraats, Suze Valen & Tos T.J.M. Berendschot) Apr. 30, 2005—(1 page).

(Continued)

*Primary Examiner* — Mohammed A Hasan
(74) *Attorney, Agent, or Firm* — Nixon Peabody LLP

(57) ABSTRACT

A reflectometry instrument includes a light source for emitting an illumination beam that illuminates the macula. A portion of the illumination beam is reflected from the macula and forms a detection beam. The detection beam is indicative of macular pigment in the macula. The instrument also includes a first mirror for reflecting the illumination beam toward the macula and for reflecting the detection beam from the macula. The instrument is configured so that the illumination beam and the detection beam remain separated between the macula and the first mirror.

17 Claims, 9 Drawing Sheets

(51) Int. Cl.
*G01J 3/02* (2006.01)
*A61B 3/15* (2006.01)
*A61B 3/00* (2006.01)
*A61B 3/14* (2006.01)
*A61B 3/10* (2006.01)

(52) U.S. Cl.
CPC .............. *A61B 3/152* (2013.01); *G01J 3/021* (2013.01); *G01J 3/0202* (2013.01); *G01J 3/0208* (2013.01); *G01J 3/0229* (2013.01); *G01J 3/0237* (2013.01); *G01J 3/42* (2013.01); *G01J 3/0218* (2013.01)

(58) Field of Classification Search
USPC ........................................................ 351/208
See application file for complete search history.

(56) References Cited

U.S. PATENT DOCUMENTS

| | | | |
|---|---|---|---|
| 5,250,965 | A | 10/1993 | Abe |
| 5,331,969 | A | 7/1994 | Silberstein |
| 6,315,412 | B1 | 11/2001 | Snodderly |
| RE38,009 | E | 2/2003 | Garnett |
| 6,572,229 | B2 | 6/2003 | Wei |
| 6,578,965 | B2 | 6/2003 | Grant |
| 6,623,117 | B2 | 9/2003 | Shibutani |
| 6,688,744 | B2 | 2/2004 | Wei |
| 6,729,728 | B2 | 5/2004 | Wei |
| 6,834,958 | B2 | 12/2004 | Cornsweet |
| 6,969,856 | B1 | 11/2005 | Hillenbrand |
| 7,156,518 | B2 | 1/2007 | Cornsweet |
| 2001/0031958 | A1 | 10/2001 | Frey |
| 2002/0097379 | A1 | 7/2002 | Goldfain |
| 2003/0004418 | A1 | 1/2003 | Marmorstein |
| 2003/0130579 | A1 | 7/2003 | McClane |
| 2005/0010115 | A1* | 1/2005 | Bone ................... A61B 3/14 600/476 |
| 2005/0182327 | A1 | 8/2005 | Petty |
| 2007/0252950 | A1 | 11/2007 | Kraats |
| 2012/0092619 | A1* | 4/2012 | Rowe .................. A61B 3/0016 351/221 |

OTHER PUBLICATIONS

"Fundus Photography for Measurement of Macular Pigment Density Distribution in Children" (Lo J. Bour, Lily Koo, Francois C. Delort, Patricia Apkarian, Anne B. Fulton) Investigative Ophthalmology & Visual Science, May 2002, vol. 43, No. 5 Copyright © Association for Research in Vision and Ophthalmology—(6 pages).
"Comparison of Fundus Autofluorescence and Minimum-Motion Measurements of Macular Pigment Distribution Profiles Derived From Identical Retinal Areas" Anthony G. Robson, Glen Harding, Frederick W. Fitzke, Jack D. Moreland "Perception" vol. 34, 2005, pp. 1027-1032—www.perceptionweb.com—(6 pages).
"Macular Pigment Assessment by Motion Photometry" Moreland JD.—MacKay Institute, Keele University, Staffordshire, ST5 5BG, UK. i.d.moreland@cns.keele.ac.uk PubMed—Arch Biochem Biophys. Oct. 15, 2004; 430(2):143-8—(1 page).
"Macular Pigment Optical Density Measurement: A Novel Compact Instrument" Stephen Beatty, Hui-Hiang Koh, David Carden and Ian J. Murray, Ophthal. Physical Opt. vol. 20, No. 2, pp. 105-111, 2000 © 2000 The College of Optometrists, Published by Elsevier Science Ltd. Printed in Great Britain—(7 pages).
"A Practical Method for Measuring Macular Pigment Optical Density" Billy R. Wooten, Billy R. Hammond, Jr., Richard I. Land and D. Max Snoddderly Investigation Ophthalmology and Visual Science. 1999;40:2481-2489. © 1999 by The Association for Research in Vision and Ophthalmology, Inc.—(14 pages).
"Macular Pigment Measurement by Heterochromatic Flicker Photometry in Order Subjects: The Carotenoids and Age-Related Eye Disease Study" D. Max Snodderly, Julie A. Mares, Billy R. Wooten, Lisa Oxton, Michael Gruber, and Tara Ficek, for the AREDS Macular Pigment Study Group Investigative Ophthalmology & Visual Science, Feb. 2004, vol. 45, No. 2 Copyright © Association for Research in Vision and Ophthalmology.—(8 pages).
"Macular Pigment" Property of the University of Westminster, Vision Research Group John Mellerio—mellerj@wmin.ac.uk—(10 pages).
"Heterochromatic Flicker Photometry" Department of Physics, Florida International University, Miami 33199, USA Bone RA, Landrum JT.—bone@fin.edu PubMed—Arch Biochem Biophys. Oct. 15, 2004;430(2):137-42—(1 page).
"A Portable Instrument for Measuring Macular Pigment With Central Fixation" Mellerio J, Ahmadi-Lan S, van Kuijk F, Pauleikhoff D, Bird A, Marshall J.—(1 page).
"Macular Pigment Density Measured by Autofluorescence Spectrometry: Comparison with Reflectometry and Heterochromatic Flicker Photometry" Delori FC, Goger DG, Hammond BR, Snodderly DM, Burns SA. Schepens Eye Research Institute, Boston, Massachusetts 02114, USA. PubMed—Opt Soc Am a Opt Image Sci Vis. Jun. 2001;18(6):1212-30.—(1 page).
"Autofluorescence Method to Measure Macular Pigment Optical Densities Fluorometry and Autofluorescence Imaging" Francois C. Delori Schepens Eye Research Institute and Harvard Medical School, Boston, M.A. USA © 2004 Published by Elsevier Inc.—(7 pages).
"Resonance Raman Measurement of Macular Carotenoids in the Living Human Eye" Paul S. Bernstein, Da-You Zhao, Mohsen Sharifzadeh, Igor V. Ermakov , Werner Gellermann Department of Ophthalmology and Visual Sciences, Moran Eye Center, University of Utah School of Medicine, Salt Lake City, UT, USA, Department of Physics, University of Utah, Salt Lake City, UT © 2004 Elsevier Inc.—(7 pages).
"Influence of Lutein Supplementation on Macular Pigment, Assessed with Two Objective Techniques" Tos T. J. M. Berendschot, R. Alexandra Goldbohm, Wilhelmina A. A. Klöpping, Jan van de Kraats, Jeannette van Norel, and Dirk van Norren © 2000 by the Association for Research in Vision and Ophthalmology, Inc.—(1 page).
"Influence of Lutein Supplementation on Macular Pigment, Assessed With Two Objective Techniques" Berendschot TT, Goldbohm RA, Klopping WA, van de Kraats J, van Norel J, van Norren D. University Medical Centre Utrecht, Department of Ophthalmology, The Netherlands PubMed—Invest Ophthal Vis. Sci. Oct. 2000; 41(11):3322-6.—(1 page).
"Objective Determination of the Macular Pigment Optical Density Using Fundus Reflectance Spectroscopy" Tos T.J.M. Berendschot and Dirk van Norren Department of Ophthalmology, University Medical Center Utrecht, The Netherlands © 2004 Elsevier, Inc.—(7 pages).
"Current Concepts in the Pathogenesis of Age-Related Macular Degeneration" Marco A. Zarbin, MD, PhD. Arch Ophthalmol./vol. 122. Apr. 2004—www.archophthalmol.com © 2004 American Medical Association.—(17 pages).
"Assessment of the Validity of In Vivo Methods of Measuring Human Macular Pigment Optical Density" Hammond BR Jr., Wooten BR, Smollon B. Vision Science Laboratory, University of Georgia, Athens, Georgia 30602-3013, USA PubMed—Optom Vis. Sci. May 2005; 82(5):387-404—(1 page).
In Vivo Assessment of Retinal Carotenoids: Macular Pigment Detection Techniques and Their Impact on Monitoring Pigment Status Joanne Curran Celentano, Joanne D. Burke and Billy R Hammond, Jr. Department of Animal and Nutritional Sciences, University of New Hampshire, Durham, NH and Department of Psychology and Behavior Sciences, University of Georgia, Athens, GA © 2002 American Society for Nutritional Sciences—(5 pages).
"Macular Degeneration—The Latest Scientific Discoveries and Treatments for Preserving Your Sight" Robert D'Amato, M.D., Ph.D., and John Snyder Copyright © 2000 by Robert d'Amato and Joan Snyder—(2 pages).
"Age-Related Macular Degeneration" Jeffrey W. Gerger, Stuart L. Fine and Maureen G. Maguire, Mosby, 1999.Jul. 2002 / 576 pp, illus. /ISBN: 08247-0682-X—(3 pages).

(56) References Cited

OTHER PUBLICATIONS

J. van. de. Kraats, T.T.J.M. Berendschot, and D. van Norren, "The pathways of light measured in fundus reflectometry," Vision Res. 36, 2229-2247 (1996)—(19 pages).

F.C. Delori and K.P. Pfibsen, "Spectral reflectance of the human ocular fundus," Appl. Opt. 28, 1061-1077 (1989)—(17 pages).

V.P. Gabel, R. Birngruber, and F. Hillenkamp, "Visible and near infrared light absorption in pigment epithelium and choriod," in *Excerpta Medica, International Congress Series* No. 450, K. Shimizu and J.A. Oosterhuis, eds, (Elsevier, Amsterdam, 1978), pp. 658-662—(4 pages).

G.J. Handelman, D.M. Snodderly, N.I. Krinsky, M.D. Russett, and A.J. Alder, "Biological control of primate macular pigment. Biochemical and densitometric studies," Invest. Ophthalmol. Vis. Sci. 32, 257-267 (1991)—(11 pages).

J. Pokorny, V.C. Smith, and M. Lutze, "Aging of the human lens," Appl., Opt. 26, 1437-1440 (1987)—(4 pages).

O.W. van Assendelft, *Spectroscopy of hemoglobin derivatives*, C.C. Thomas ed., (C.C. Thomas, Springfield, IL, 1979), pp. 54-57—(2 pages).

D. van Norren and L. F. Tiemeijer, "Spectral reflectance of the human eye," Vision Res. 26, 313-320 (1986)—(8 pages).

"Fundus Photography for Measurement of Macular Pigment Density Distribution in Children" Lo J. Bour, Lily Koo, Francois C. Delori, Patricia Apkarian, and Anne B. Fulton—Investigative Ophthalmology & Visual Science, May 2002, vol. 43, No. 5—(6 pages).

"Macular Pigment Assessment by Motion Photometry" J.D. Moreland—MacKay Institute, Keele University, Staffordshire, UK—Archives of Biochemistry and Biophysics 430 (2004) 143-148—(6 pages).

"Heterochromatic Flicker Photometry" Richard A. Bone and John T. Landrum—Department of Physics, Department of Chemistry & Biochemistry, Florida International University, Miami, Florida—Archives of Biochemistry and Biophysics 430 (2004) 137-142—(6 pages).

"A Portable Instrument for Measuring Macular Pigment with Central Fixation" J. Mellerio, S. Ahmadi-Lari, F.J.G.M. van Kuijk, D. Pauleikhoff, A.C. Bird and J. Marshall—Current Eye Research—2002, vol. 25, No. 1, 37-47—(11 pages).

"Macular Pigment Density Measured by Autofluorescence Spectrometry: Comparison with Reflectometry and Heterochromatic Flicker Photometry" Francois C. Delori, Douglas G. Goger, Billy R. Hammond, D. Max Snodderly and Stephen A. Burns—Schepens Eye Research Institute, Boston, MA and Harvard Medical School, Boston, MA—J. Opt. Soc. Am. A, vol. 18, No. 6, Jun. 2001—1212-1230—(19 pages).

"Influence of Lutein Supplementation on Macular Pigment, Assessed with Two Objective Techniques" Tos. T. J. M. Berendschot, R. Alexandra Goldbohm, Wilhelmina A. A. Klöpping, Jan van de Kraats, Jeannette van Norel and Dirk van Norren—Investigative Ophthalmology & Visual Science, Oct. 2000, vol. 41, No. 11—(5 pages).

"Assessment of the Validity of in Vivo Methods of Measuring Human Macular Pigment Optical Density" Billy R. Hammond, Jr., Billy R. Wooten and Bill Smollon—University of Georgia, Athens, GA and Brown University, Providence, RI—Optometry and Vision Science, vol. 82, No. 5, May 2005—(17 pages).

International Search Report in International Application No. PCT/US2007/009636, dated May 27, 2008—(3 pages).

Written Opinion in International Application No. PCT/US2007/009636, dated May 27, 2008—(3 pages).

Extended European Search Report in European Patent Application No. 07755780.9, dated Oct. 15, 2013—(8 pages).

International Search Report and Written Opinion in International Patent Application No. PCT/US2018/016658, dated May 14, 2018 (17 pages).

\* cited by examiner

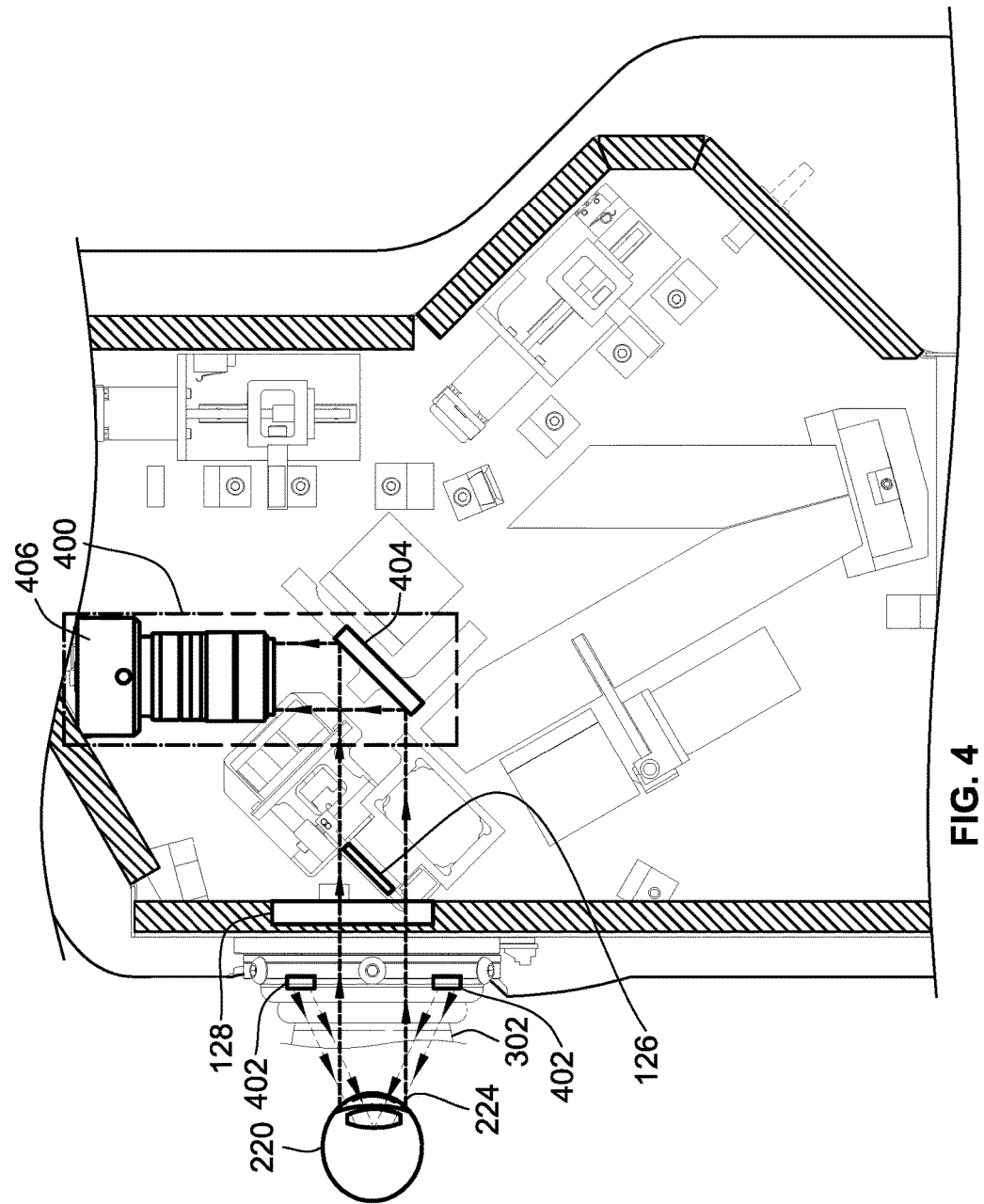

REFLECTOMETRY INSTRUMENT AND METHOD FOR MEASURING MACULAR PIGMENT

CROSS-REFERENCE TO RELATED APPLICATION(S)

The present application claims the benefit of and priority to U.S. Provisional Patent Application No. 62/464,028, filed Feb. 27, 2017, entitled "REFLECTOMETRY INSTRUMENT AND METHOD FOR MEASURING MACULAR PIGMENT," which is hereby incorporated by reference herein in its entirety.

FIELD OF THE INVENTION

The present invention relates to a reflectometry instrument that measures characteristics of the patient's eye, such as macular pigment, with a high degree of accuracy and without dilating the patient's pupil.

BACKGROUND OF THE INVENTION

The retina is the layer of nerve cells at the back of the eye, which convert light into nerve signals that are sent to the brain. In humans, and in other primates (but not in most other mammals, or other types of animals), the retina has a small yellowish area in the center of the field of vision. That yellowish area is called the "macula." It provides fine-resolution vision in the center of the visual field and is essential to good vision. People who suffer from macular degeneration often lose the ability to read, recognize faces, drive, or walk safely on unfamiliar routes.

The surrounding portions of the macula can only provide coarse resolution. This physiological feature limits and controls the number of nerve signals that the brain must rapidly process, to form coherent rapid-response vision, and it also helps limit and control the huge number of rod and cone receptors that the eye must continually regenerate and recycle, every day. Many people do not realize the retina can provide only coarse resolution, outside of a limited central area, because the eyes and the brain have developed an extraordinary ability to synthesize coherent vision from a combination of fine and coarse resolution. During that type of vision synthesis, the eye muscles cause the eyes to flit back and forth over a larger field of vision, pausing at each location for just an instant while the eye quickly "grabs" a fine-resolution image of a limited area. This process occurs so rapidly that a person does not notice it happening, and does not pay attention to how a complete visual image and impression is being assembled and updated from combinations of fine and coarse resolution images.

There is also a peculiar anatomic structure in the retinas of humans, which points out the difference between fine resolution (provided by the macula) and coarse resolution (provided by the remainder of the retina). In humans, the blood vessels that serve the retina actually sit in front of the retina, where they can block and interfere with incoming light, before the light reaches the retina. This is counterintuitive, and one should wonder why the retina evolved with a physical handicap that literally gets in the way of good, clear vision. The answer is, in those parts of the retina, only coarse vision is being created, and blood vessels positioned in front of the retina do not interfere with that type of coarse vision. By contrast, in the macular region in the center of the retina, the blood vessels in front of the retina are lacking and supply is only from blood vessels present anywhere behind the layer of neurons with rod and cone receptors. This is consistent with the macula providing fine resolution vision, which would be blocked and hindered if the blood vessels were located in front of the neurons, in ways that would intercept and block portions of the incoming light.

"Retinal degeneration" is a descriptive term, which refers to and includes an entire class of eye diseases and disorders. It includes any progressive disorder or disease that causes the macula to gradually degenerate, to a point that substantially impairs or damages eyesight and vision. Several major categories of retinal degeneration are known. These include: (i) age-related macular degeneration, which gradually appears among some people over the age of about 65; (ii) diabetic retinopathy, in which problems with sugar and energy metabolism damage the entire retina, including the macula; (iii) eye diseases that affect the macula due to gene and/or enzyme defects, such as Stargardt's disease, Best's disease, Batten's disease, Sjogren-Larsson syndrome; and (iv) various other eye disorders that lead to gradual degeneration of the macula (and possibly other parts of the retina) over a span of time. This is not an exclusive list, and other subclasses and categories also are known. For example, age-related macular degeneration is subdivided into wet and dry forms, depending on whether abnormal and disruptive blood vessel growth is occurring in the structural layers behind the retina.

The causes and effects of macular degeneration, and efforts to prevent or treat it, are described in numerous books (e.g., "Macular Degeneration," by Robert D'Amato et al (2000) and "Age-Related Macular Degeneration," by Jennifer Lim (2002)), articles ("Age-Related Macular Degeneration" by Berger et al (1999)) and patents, such as U.S. Pat. No. Re. 38,009, which is assigned to ZeaVision LLC, and is incorporated by reference in its entirety.

To address problems associated with retinal degeneration in a patient, instruments are needed to help measure the macular pigment within the patient's eye. While various instruments exist that can perform this function, improvements are needed to provide instruments that are more accurate, easier to use, and less time consuming. For example, many instruments require the eye to be dilated before use, which can be uncomfortable to the patient and add extra time and cost to the procedure.

The present invention is directed to an improved reflectometry instrument that can measure the macular pigment within the eye of the patient without the need to dilate the eye. The improved reflectometry also provides the ability to measure the various constituents of the macular pigment, including lutein and zeaxanthin.

SUMMARY OF THE INVENTION

According to one aspect of the present disclosure, a reflectometry instrument is provided for illuminating a macula of a human eye. The instrument includes a light source and a first mirror. The light source emits an illumination beam that illuminates the macula. A portion of the illumination beam reflects from the macula and forms a detection beam. The detection beam is indicative of macular pigment in the macula. The first mirror reflects the illumination beam toward the macula and reflects the detection beam from the macula. The illumination beam and the detection beam remain separated between the macula and the first mirror.

According to another aspect of the present disclosure, a reflectometry instrument is provided to measure macular pigment of a macula of a human eye. The instrument includes an illumination system, a detection system, and an imaging system. The illumination system generates an illumination beam and directs the illumination beam to the macula. A detection beam is then formed, which is a portion of the illumination beam that is reflected by the macula. The illumination system directs the detection beam away from the macula. The detection system receives and measures the detection beam to determine an amount of the macular pigment in the macula. The imaging system provides a live image of the human eye prior to illuminating the human eye with the illumination beam.

According to a further aspect of the present disclosure, a reflectometry instrument is provided for illuminating a macula of a human eye. The instrument includes a light source, a spectrometer, and an afocal mirror relay. The light source emits an illumination beam that illuminates the macula. The spectrometer measures a detection beam that is a portion of the illumination beam reflected from the macula. The detection beam is indicative of the amount of macular pigment in the macula. The afocal mirror relay reflects the illumination beam from the light source and toward the macula and reflects the detection beam from the macula and toward the spectrometer. The illumination beam and the detection beam reflect off each mirror of the afocal mirror relay offset from each other to remain separated after the macula.

According to yet another aspect of the present disclosure, a method of determining the amount of macular pigment in the macula of a human eye is disclosed. The method includes the act of directing an illumination beam from an illumination source and onto the macula via a series of mirrors so as to produce a detection beam that reflects from the macula. The method further includes the act of directing the detection beam from the macula and to a spectrometer via the series of mirrors. The detection beam reflects off the series of mirrors offset from the illumination beam such that the detection beam and the illumination beam remain separated. The method further includes the acts of receiving the detection beam at the spectrometer, and measuring a characteristic of the detection beam at the spectrometer to determine the amount of the macular pigment.

According to a further aspect of the present disclosure, a reflectometry instrument is provided for illuminating a macula of a human eye. The instrument includes a light source for emitting an illumination beam to illuminate the macula. A portion of the illumination beam is then reflected from the macula and forms a detection beam. The detection beam is indicative of macular pigment in the macula. The instrument further includes a plurality of mirrors in series for reflecting the illumination beam toward the macula and for reflecting the detection beam from the macula. The instrument is configured so that the illumination beam and the detection beam remain separated between each mirror of the plurality of mirrors.

According to additional aspects of the present disclosure, a reflectometry instrument is provided to measure macular pigment of a macula of a human eye. The instrument includes an illumination system for generating an illumination beam and directing the illumination beam to the macula. As a result, a detection beam is generated as a portion of the illumination beam reflected by the macula. The instrument also includes a detection system for receiving and measuring the detection beam to determine an amount of the macular pigment in the macula, and a camera for obtaining a live image of the human eye prior to, during, or after directing the illumination beam to the macula. The instrument also includes an electronic display for presenting the live image of the human eye to an operator of the reflectometry instrument. The electronic display presents a reticle overlaid in the live image of the human eye for the operator to align the human eye with the illumination beam.

According to other aspects of the present disclosure, a reflectometry instrument is provided for illuminating a macula of a human eye. The instrument includes an illumination system for emitting an illumination beam to illuminate the macula, and a spectrometer for measuring a detection beam. The detection beam is a portion of the illumination beam that is reflected from the macula and is indicative of the amount of macular pigment in the macula. The instrument also includes an afocal mirror relay for reflecting the illumination beam from the light source and toward the macula and for reflecting the detection beam from the macula and toward the spectrometer. The reflectometry instrument is configured to obtain and process at least 100 images of the macula per second for measuring the amount of the macular pigment.

According to still further aspects, a reflectometry instrument is provided to measure macular pigment of a macula of a human eye. The instrument includes a housing having an illumination system, a detection system, and a beam dump. The illumination system is configured to generate an illumination beam and direct the illumination beam to the macula. A detection beam is generated as a portion of the illumination beam reflected by the macula. The detection system is configured to receive and measure the detection beam to determine an amount of the macular pigment in the macula. The beam dump is in optical alignment with an optical input of the detection system for absorbing stray light within the reflectometry instrument. The instrument also includes an eyepiece connected to the housing, which is configured to interface with the human eye to prevent ambient light from entering the housing. The beam dump and the eyepiece allow the reflectometry instrument to measure the macular pigment of the macula in a lit environment.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 4 is a schematic of an imaging system within a reflectometry instrument according to aspects of the present disclosure.

DETAILED DESCRIPTION

Figure 1:
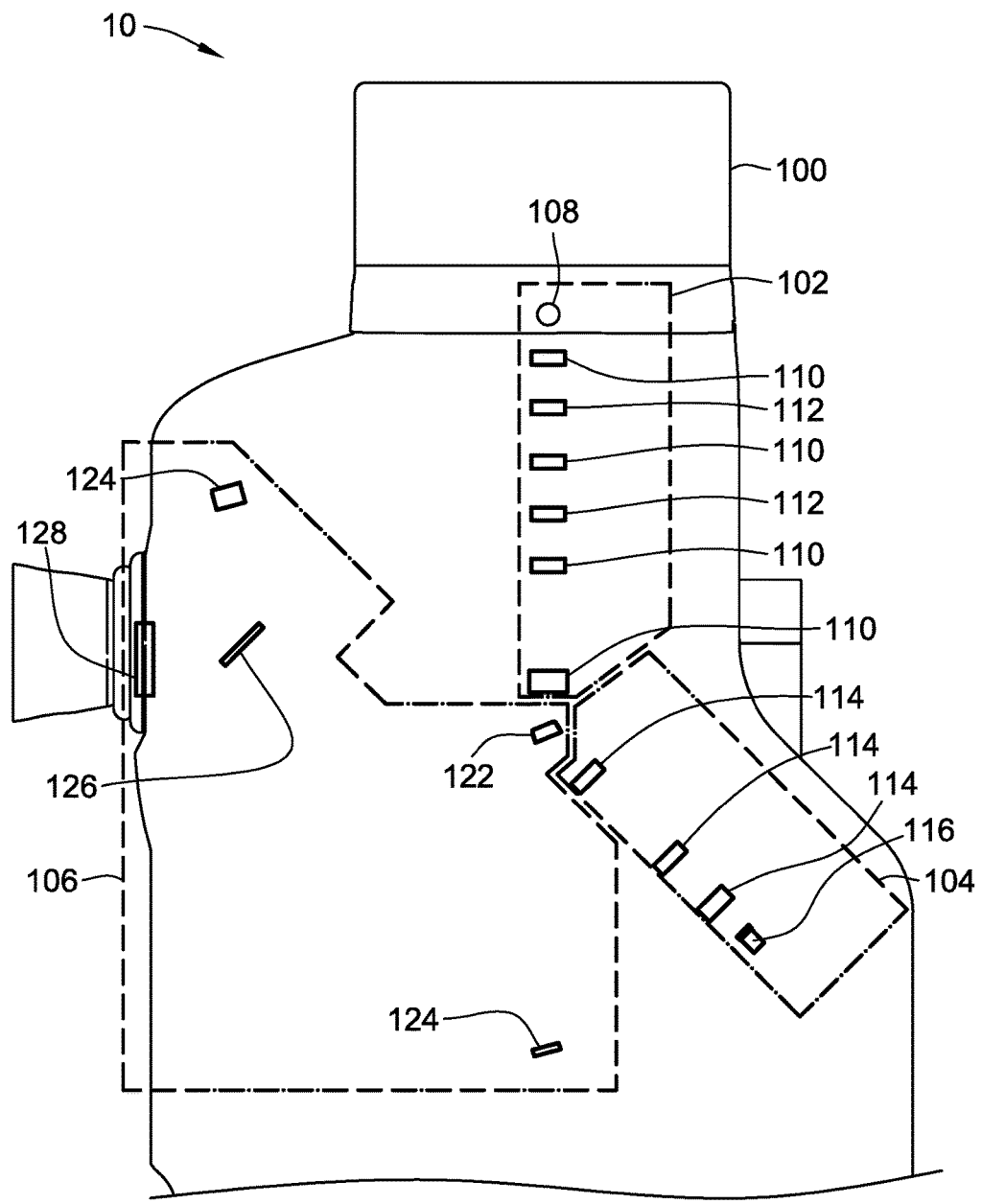
FIG. 1 is schematic of the internal components of a reflectometry instrument according to aspects of the present disclosure.

FIG. 1 illustrates a reflectometry instrument 10 adapted to measure characteristics of a human eye. The reflectometry instrument 10 will be described in reference to three main systems: an illumination system 102, a detection system 104, and a separation system 106, all of which are contained within an upper housing 100 of the reflectometry instrument 10. The illumination system 102 includes a light source 108, a plurality of lenses 110, and a plurality of masks 112. The illumination system 102 generates an illumination beam having certain characteristics that will be transmitted to the patient's eye. As mentioned above, the reflectometry instrument 10 may be used on an un-dilated pupil, making the instrument 10 much easier to use and decreasing the time required to test a patient's eye.

The detection system 104 includes a plurality of lenses 114 and a fiber optic cable 116. The detection system 104 receives a detection beam, which is a portion of the illumination beam that is reflected off the patient's eye, and transmits the detection beam to an instrument for analyzing the detection beam. In some aspects, the instrument is a spectrometer 118. The spectrometer 118 can optionally be considered part of the detection system 104 or be considered a separate component from the detection system 104, such as a separate system contained within the upper housing 100.

The separation system 106 includes a D-shaped mirror 122, a plurality of mirrors 124, and a dichroic fold mirror 126. The separation system 106 can also include a window 128. Alternatively, the window 128 can be considered a general component of the instrument 10, such as part of the upper housing 100 and not part of the separation system 106. The separation system 106 is used for providing the illumination beam to the patient's eye and for receiving the detection beam that is returned from the patient's eye.

The detection beam has an energy level orders of magnitude less than the illumination beam. Thus, as discussed in more detail below, the separation system 106 keeps the illumination beam and the detection beam substantially separated and distinct, which limits the various "ghost images" and/or reflections that can be present from the interaction of the illumination beam as it reflects off of the various components adjacent to the detection beam. "Ghost images" are created on optical systems due to the reflections at surfaces. In particular, ghost images are formed by Fresnel reflections from refractive surfaces. For example, light reflected from the (inner) surfaces of lenses may be reflected again to form reasonably well defined images.

In prior art reflectometry systems, the reflections and ghost images were not as big of a problem because a dilated pupil was required, yielding a stronger output signal of the detection beam. In the present disclosure, two distinct paths (i.e., avoidance of overlap) are used for the illumination beam and the detection beam within the separation system 106. If the illumination beam and the detection beam are not kept separate and distinct, then the illumination beam can affect the characteristics of the detection beam before it is received by the detection system 104, and more particularly the fiber optic cable 116 and spectrometer 118 for processing. The details of the paths of the illumination beam and the detection beam within the reflectometry instrument 10 are shown in FIGS. 2A-2C.

Figure 2A:
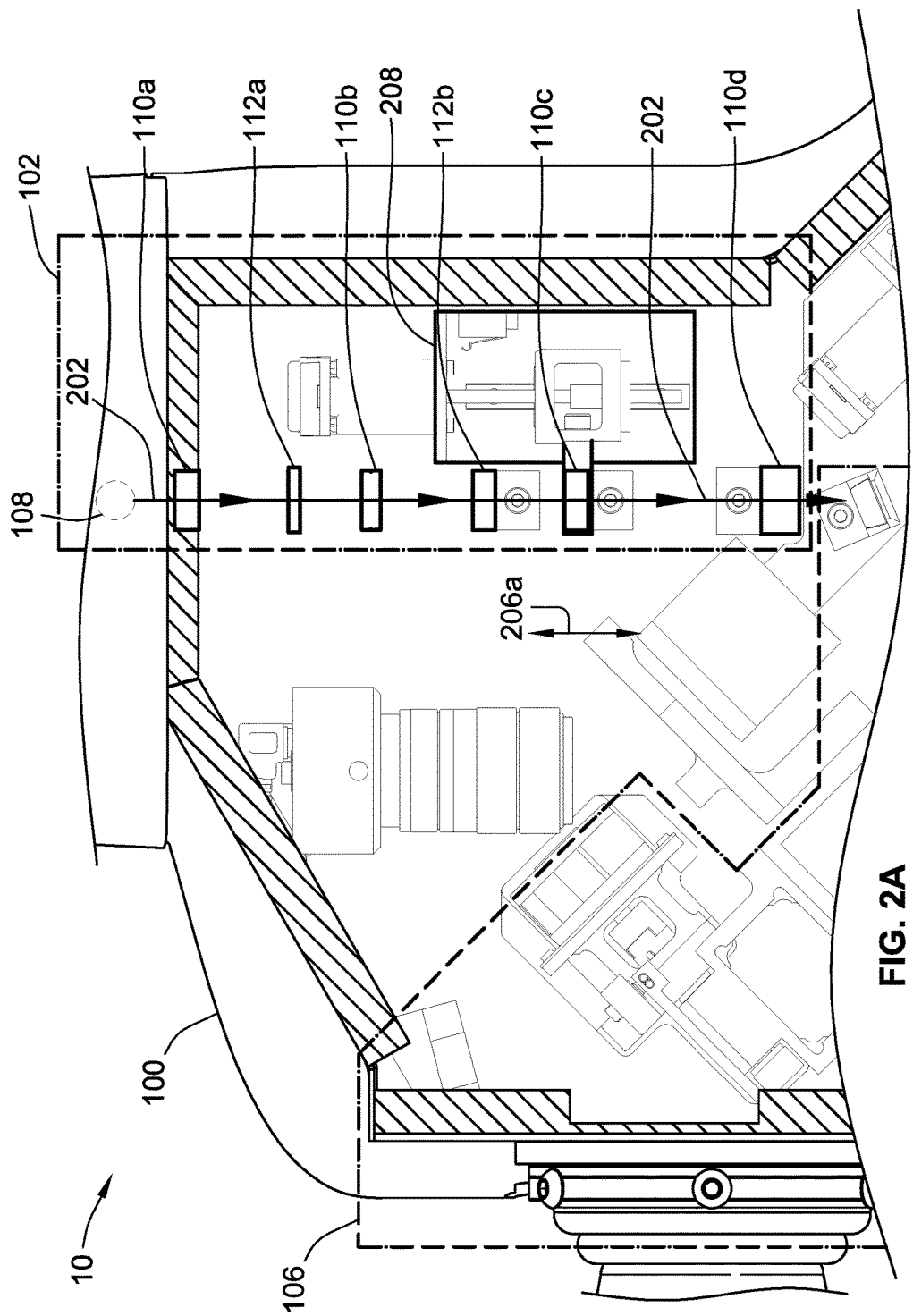
FIG. 2A is a schematic of an illumination system within a reflectometry instrument according to aspects of the present disclosure.
Figure 2B:
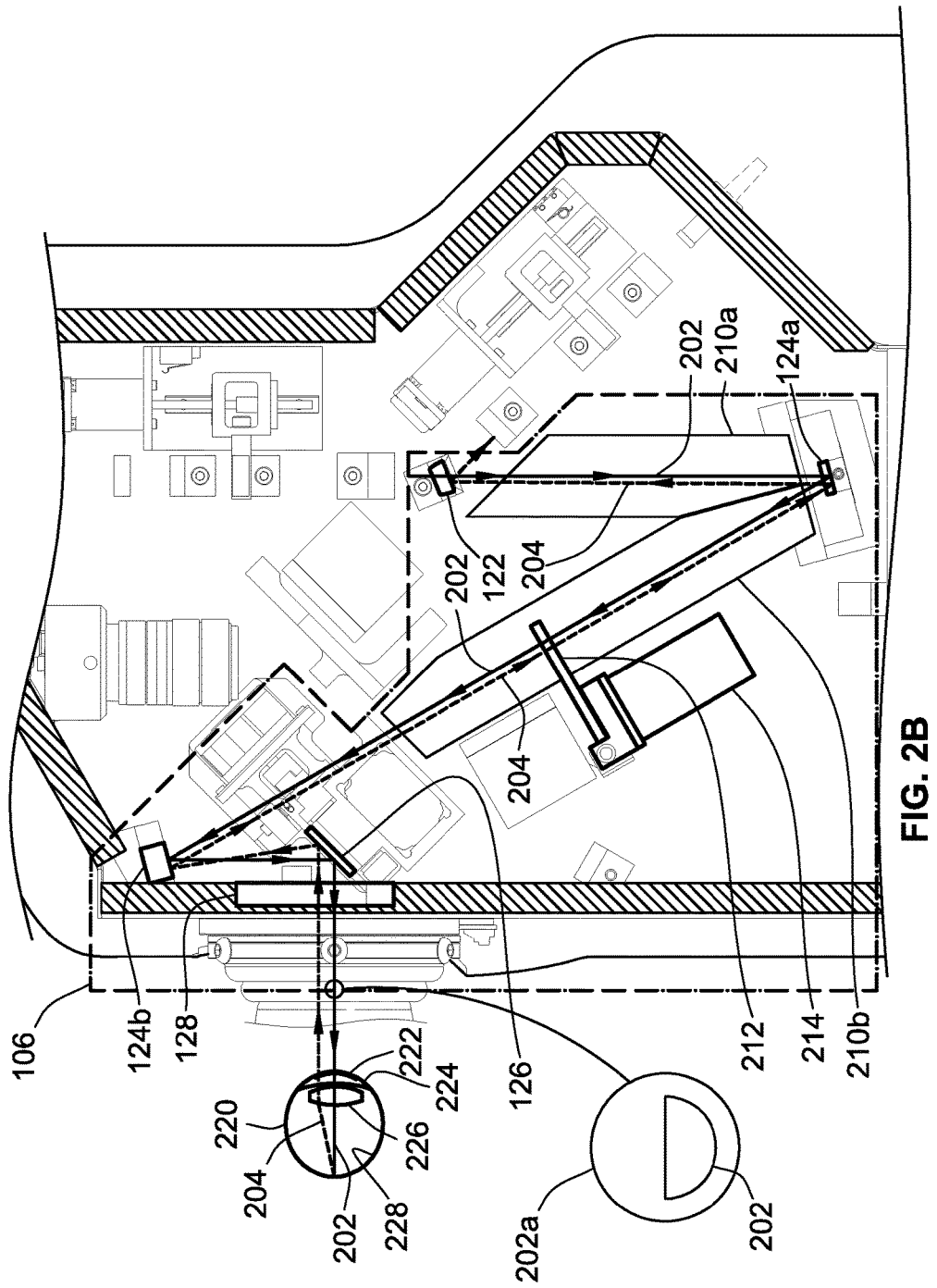
FIG. 2B is a schematic of a detection system within a reflectometry instrument according to aspects of the present disclosure.
Figure 2C:
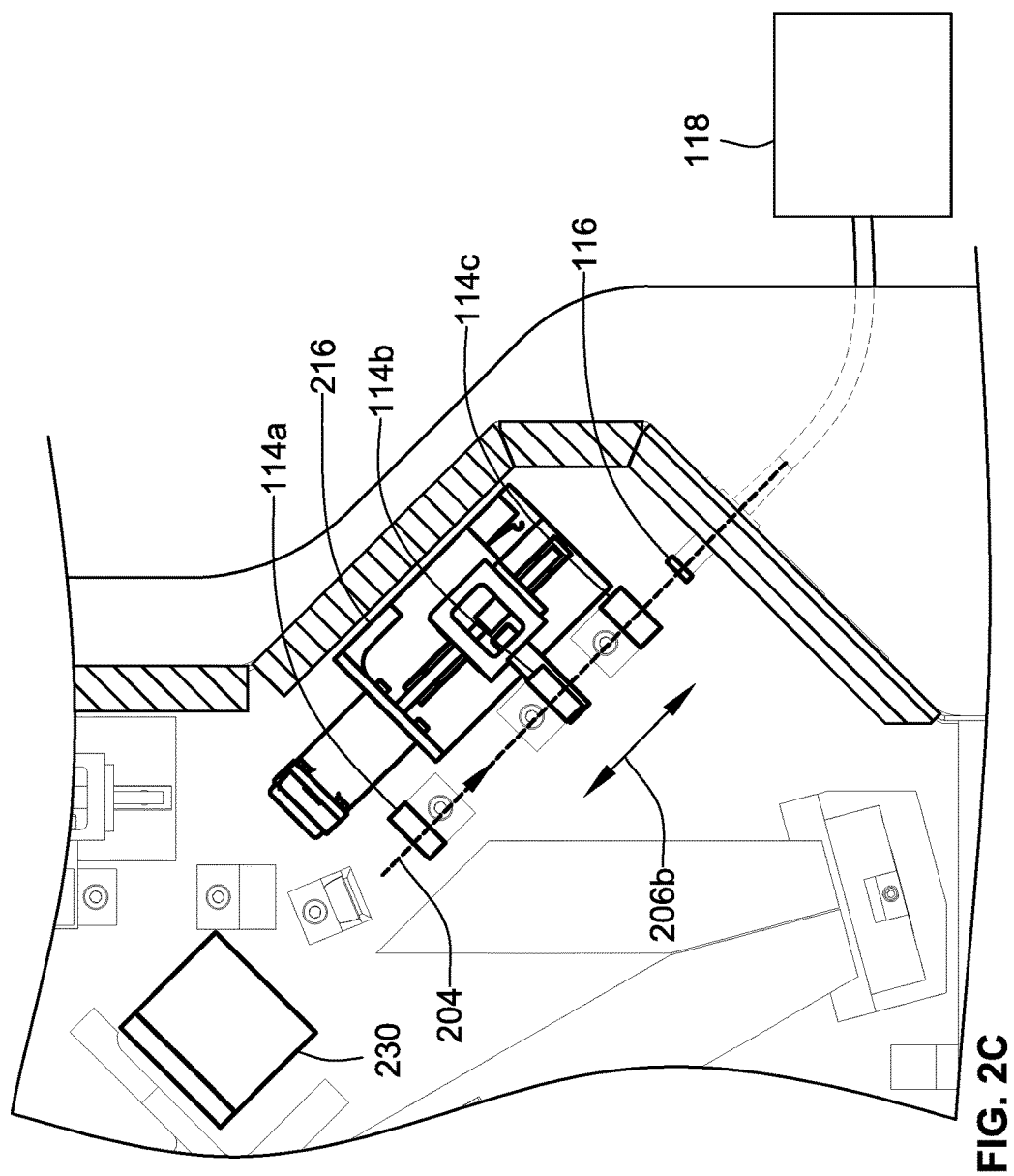
FIG. 2C is a schematic of a separation system within a reflectometry instrument according to aspects of the present disclosure.

Referring to FIG. 2A, the light source 108 is provided at one end of the illumination system 102. The light source 108 is adapted to emit a beam of light, such as white light. The light source 108 can be a tungsten halogen light source, such as a low voltage 100 W halogen lamp, without a reflector, manufactured by OSRAM (part number 64623 HLX). However, other light sources may also be used, such as white-light light-emitting diodes (LEDs). The beam emitted from the light source 108 is altered by the components in the illumination system 102, as discussed below. The beam, which eventually enters the human eye, is referred to herein as the "illumination beam" (i.e., represented by the solid line 202).

After being emitted from the light source 108, the illumination beam encounters the first lens 110a. In some aspects, the lens 110a can include an anti-reflective coating to allow only light from about the 400-1000 nm range to transmit through the lens and allow for less than about 1% of the light to reflect within the same range.

Continuing from the first lens 110a, the illumination beam 202 encounters a retinal mask 112a. The retinal mask 112a is placed at the focus of the first lens 110a to limit the illumination of the retina of the patient's eye to 1 degree. The retinal mask 112a can consist of an opening (e.g., a 2 mm×1 mm opening) through which the illumination beam 202 may travel. Here, unwanted reflections of the glass envelope of the light source 108, and other unwanted stray light sources, are cut off to leave a clean, well-defined illumination beam 202 profile.

After the retinal mask 112a, the illumination beam 202 encounters a second lens 110b. The second lens 110b can similarly include the anti-reflective coating as the first lens 110a.

Continuing from the second lens 110b, the illumination beam 202 encounters a pupil mask 112b. The pupil mask 112b shapes the illumination beam 202 into a semicircular pattern. Specifically, the pupil mask 112b has a generally semi-circular shape and determines the shape of the illumination beam 202 as it enters the pupil of the patient's eye. The general profile of the illumination beam 202 as it enters the eye is illustrated in FIG. 2B.

After the pupil mask 112b, the illumination beam 202 encounters a third lens 110c and a fourth lens 110d, which form a reflective afocal relay. The third lens 110c is configured to translate (i.e., as represented by the double arrows 206a) along the optical axis of the illumination beam 202 to focus the illumination beam 202 on the retina of the patient's eye and allow the eye to focus on the retinal mask 112a for compensating for the refractive error of the patient's eye. The illumination system 102 includes a translation system 208 that is attached to the third lens 110c and is configured to translate the third lens 110c. The lenses 110c and 110d can be similar to the lenses 110a and 110b, but other lenses may be used as well. After the lens 110d, the illumination beam 202 exits the illumination system 102 and enters the separation system 106, discussed in greater detail below.

One type of lens that may be used for the lenses 110a-110d is the Edmund Optics 49-323 achromatic lens manufactured by Edmund Optics. The detailed specifications of this lens are as follows: Paraxial Focal Length—25 mm±2%; Diameter—12.5+0/−0.025 mm; Clear Aperture—12.6 mm; Center Thickness ($t_c$)—6.25±0.2 mm; Edge Thickness ($t_e$)—4.9 mm; Material—Crown and flint glasses; Surface Quality—40-20 scratch and dig; Cement—Ultra-violet-cured polyester; Centration—3 arc minutes; and an AR coating VIS-NIR (Edmund Optics broadband coating). The lenses 110a-110d are short focal achromatic lenses with large diameters versus focal length (high speed). These "high-speed" lenses are especially useful if it is desired to have the target of the illumination beam 202 located at peripheral retinal sites and light for a separate fixation target pass through more eccentric parts of the lenses 110a-110d of the illumination system 102.

In summary, the illumination system 102 helps to establish some of the characteristics of the illumination beam 202 necessary for measuring the macular pigment of a patient's eye. As illustrated, the illumination system 102 is shown as being generally perpendicular to the direction of the illumination beam 202 as the illumination beam 202 enters the patient's eye. However, the illumination system 102 may be at other angles as well depending on the arrangement of the optical components within the reflectometry instrument 10.

Referring now to FIG. 2B, the illumination beam 202 encounters the separation system 106 after passing through the lens 110d and exiting the illumination system 102. Within the separation system 106, the illumination beam 202 first encounters the D-shaped mirror 122. As named, the D-shaped mirror 122 is generally formed in the shape of the capital letter "D." This shape allows the D-shaped mirror 122 to have the illumination beam 202 pass by without interacting with the illumination beam 202, while also being in the path of the detection beam, described below.

Continuing toward the patient's eye, the illumination beam 202 next encounters mirrors 124a and 124b. The mirrors 124a and 124b form an afocal relay and are configured to reflect the illumination beam 202 towards the dichroic fold mirror 126. The mirrors 124a and 124b can have coatings to accommodate larger wavelengths. In some aspects, the mirrors 124a and 124b can be coated with protected silver allowing for >96% reflectivity over the 400-1000 nm spectrum of interest. The mirrors 124a and 124b are used in an off-axis manner to allow the illumination beam 202 and the detection beam (described below) to be un-obscured. The use of the mirrors 124a and 124b for the afocal relay eliminates ghost reflections, which improves the signal to noise ratio at the spectrometer 118.

The mirror 124a is positioned at the convergence of two tubes 210a and 210b. In some aspects, the tubes 210a and 210b can be void of other components. Alternatively, the tubes 210a and 210b can contain one or more components for shaping or otherwise affecting the illumination beam 202 and the detection beam. In some aspects, these components can include one or more filters (e.g., filter 212). The filter 212 can be configured to move into and out of the path of the illumination beam 202 to control the intensity of the illumination beam 202 reaching the patient's eye. For example, the reflectometry instrument 10 can include a device 214 (e.g., servo, motor, actuator, or the like attached to an arm or lever that holds the filter 212) that controls the position of the filter 212, i.e., in or out of the path of the illumination beam 202.

In use, the reflectometry instrument 10 is first aligned with the patient and the patient adjusts the components, as described herein, to accommodate for the patient's diopter. During this alignment and configuration period, the illumination beam 202 interacting with the patient's eye does not need to be as intense as it does during analysis of the patient's macula. Accordingly, during alignment and configuration, one or more of the filters contained within the tubes 210a and 210b, such as the filter 212, can be placed within the path of the illumination beam 202 to reduce its intensity. After alignment and configuration are completed and the analysis portion of an examination is to begin, the one or more filters can be removed from the path of the illumination beam 202 to allow the full intensity of the illumination beam 202 to illuminate the patient's eye for the examination. The one or more filters (i.e., filter 212) can include, for example, an ND filter with an optical density of 2.0 manufactured by Thorlabs, Inc. (part number ND520B).

One or more other filters within the tubes 210a and 210b also can be adapted to cut off light energy in the ultra-violet (UV) range and/or light energy in infrared range. One type of UV filter adequate for use as a filter is a 25 mm round Schott GG395 filter of 3 mm thickness. One type of IR filter adequate for use as a filter is a 25 mm round Schott KG2 filter of 3 mm thickness. It should be noted that an infrared filter may not be needed since the level of infrared light leaving the light source 108, such as a halogen lamp, is typically not harmful to the patient's eye and will not affect the measurement of the light-absorbing constituents in the eye.

The dichroic fold mirror 126 is configured to reflect the illumination beam 202 through the window 128 and into the patient's eye. The dichroic fold mirror 126, therefore, is made of a material that reflects the light of the illumination beam 202. Once reflected off the dichroic fold mirror 126, the illumination beam 202 is suited to enter the eye 220 and is shaped according to the shape of the illumination beam 202 in the callout 202a.

The illumination beam 202 passes through the cornea 222, the pupil 224, and the lens 226 in the eye 220. The pupil 224, which does not need to be dilated to use the reflectometry instrument 10, controls the amount of ambient light that enters the patient's eye 220. The illumination beam 202 continues toward the retina 228 in the eye. Upon reaching the retina 228 (and macula), a portion of the illumination beam 202 is reflected from the macula towards the lens 226 and the cornea 222 as the detection beam 204. The illumination beam 202 and the detection beam 204 are separated in the frontal parts of the eye 220 (i.e., the cornea 222 and the lens 226). The separation is typically about 0.7 mm in the frontal parts of the eye.

Once through the frontal parts of the eye 220, the detection beam 204 then proceeds back toward the window 128 and to the dichroic fold mirror 126. The detection beam 204 reflects off the dichroic fold mirror 126 and encounters the mirrors 124a and 124b. However, the detection beam 204 reflects off the dichroic fold mirror 126 and the mirrors 124a and 124b at locations offset from the locations of the illumination beam 202. In some aspects, the illumination beam 202 and the detection beam 204 are parallel within the separation system 106 so that the two beams do not interact. The offset nature of the reflections and parallel nature of the beams 202 and 204 prevents or at least reduces interactions between the illumination beam 202 and the detection beam 204 that could affect the characteristics of the detection beam 204 used to determine information on the patient's eye, such as the amount of macular pigment within the macula of the eye. Thus, keeping the illumination beam 202 and the detection beam 204 separated allows the patient's eye 220 to be examined without dilating the pupil 224, among other advantages.

As illustrated in FIG. 2B, the detection beam 204 remains separated from the illumination beam 202 as the detection beam 204 reflects off of the mirrors 124a and 124b toward the spectrometer 118. The detection beam 204 reflects off the mirrors 124a and 124b at a distance of about 1.4 mm to about 2.8 mm from the centers of the mirrors 124a and 124b. While the separation is about 0.7 mm in the frontal parts of the eye, the separation in the mirrors 124a and 124b is only about 0.3 mm. This separation is only possible in combination with small retinal fields (e.g., 1 degree as used herein). If the light paths (both for the illumination beam 202 and detection beam 204) from this small retinal field are drawn from the retina through the eye optics and through the mirrors 124a and 124b, they are always separated in the optics with this design, keeping first-order backscatter reflection from these layers from the illumination beam 202 into the detection beam 204 zero.

Continuing toward the detection system 104, the detection beam 204 next encounters the D-shaped mirror 122. The mirrors 124a and 124b and the dichroic fold mirror 126 are configured to direct the detection beam 204 to reflect off the D-shaped mirror 122. Thus, unlike the illumination beam 202, which passes by and does not interact with the D-shaped mirror 122, the detection beam 204 reflects off the D-shaped mirror 122 towards the detection system 104. After reflecting off the D-shaped mirror 122, the detection beam 204 exits the separation system 106.

Referring now to FIG. 2C, after exiting the separation system 106, the detection beam 204 enters the detection system 104. Initially, within the detection system 104, the detection beam 204 encounters the lenses 114a and 114b. The lenses 114a and 114b form an afocal relay. Further, the lens 114b is configured to be translated along the optical axis of the detection beam 204 in the direction of the double arrows 206b. Translation of the lens 114b adjusts for the refractive error of the patient's eye, thus eliminating or reducing defocus and minimizing the size of the focal spot of the detection beam 204. The detection system 104 includes a translation system 216 that is attached to the lens 114b and is configured to translate the lens 114b in the motion of the double arrows 206b.

After the lens 114b, the detection beam 204 then encounters a lens 114c. The lens 114c is used for coupling the detection beam 204 into the fiber optic cable 116 that is connected to the instrument that analyzes the light, such as the spectrometer 118. The detection beam 204 is brought to a retinal image at the tip of the fiber optic cable 116 by the lens 114c. The input of the fiber optic cable 116 is in the retinal plane, and the size of the fiber optic cable 116 determines the detection field at the retina of 1 degree. In some aspects, the fiber optic cable 116 is configured to have a diameter of about 100 μm.

The lenses 114a-114c help focus the retinal image of the detection beam 204 for transmission to the fiber optic cable 116, which passes the detection beam 204 to the spectrometer 118. Because the lenses 114a-114c only provide transmission of the detection beam 204, their characteristics can be selected for the purpose of achieving a small and sharp image of the 1 degree retinal spot at the tip of the fiber optic cable 116. One example of these lenses is the Edmund Optics 49-323 achromatic lens manufactured by Edmund Optics. The detailed specifications of this lens are as follows: Paraxial Focal Length—25 mm±2%; Diameter—12.5+/−0.025 mm; Clear Aperture—12.6 mm; Center Thickness ($t_c$)—6.25±0.2 mm; Edge Thickness ($t_e$)—4.9 mm; Material—Crown and flint glasses; Surface Quality—40-20 scratch and dig; Cement—Ultraviolet-cured polyester; Centration—3 arc minutes; and AR coating VIS-NIR (Edmund Optics broadband coating).

The spectrometer 118 measures the energy of the detection beam 204 over a specific portion of the electromagnetic spectrum. More specifically, the spectrometer 118 measures the energy of the detection beam 204 at wavelength intervals that provide information about the characteristics of the eye. In some aspects, the spectrometer 118 takes a reading approximately every 0.3 nm between 330-1011 nm (about 2048 readings for each time point), which is indicative of the amount of certain constituents (e.g., macular pigment, lens pigmentation, etc.) in the patient's eyes, as described in more detail below. The spectrometer 118 can be integrated within the housing 100 or can be affixed to an exterior of the housing 100 of the reflectometry instrument 10.

In some aspects, the detection system 104 can include a beam dump 230. The beam dump 230 is positioned in optical alignment with the detection beam 204 incident on the tip of the fiber optic cable 116. More particularly, the beam dump 230 can be positioned relative to the tip of the fiber optic cable 116 such that the D-shaped mirror 122 is between the beam dump 230 and the fiber optic cable 116, with the beam dump 230, the fiber optic cable 116, and the D-shaped mirror 122 aligned with the optical axis of the detection beam 204. Positioning the beam dump 230 as described aids in preventing or reducing the elements of the lenses 114a-114c and the fiber optic cable 116 from seeing any other light reflected by the retina of the eye that may be within the reflectometry instrument 10. The reflectometry instrument 10 can also include baffles (not shown) throughout, such as within the illumination system 102, the detection system 104, and/or the separation system 106, to limit other light (e.g., ghost images of illumination beam 202 and/or detection beam 204) from illuminating unintended targets. The beam dump 230 allows, in part, for an examination using the instrument 10 to be performed in a lit environment, such as a lit office environment (e.g., a room with the lights on). In contrast, conventional instruments required that an examination be performed in a dark environment, such as with the lights off, which added to the difficulty and complexity of controlling such conventional instruments.

With the reflectometry instrument 10 as described above, and in particular the separation system 106 with the mirrors 124a and 124b, the illumination beam 202 can be kept separated from the detection beam 204. Moreover, with the mirrors 124a and 124b used instead of, for example, lenses, the amount of ghost images generated within the instrument 10 is reduced or eliminated based on the reduction in the number of surfaces the illumination beam 202 and the detection beam 204 interact with. For example, while a lens may generate a ghost image from a portion of a beam passing through the lens reflecting off the lens initially, and another portion of the beam refracting within the lens and escaping out of the lens, a mirror does not suffer from the same issue. A beam is either reflected or absorbed by the mirror. The portion absorbed by the mirror does not generate a ghost image, and the portion reflected by the mirror is the desired intent of the mirror, thus resulting in the desired reflected beam. This benefit of mirrors as compared to lenses is especially important in a beam combining relay where ghost images/reflections are substantially larger than the signal beam (illumination beam 202 versus detection beam 204) reflected by the macula. Mirrors also provide higher transmission and fewer elements when compared to an equivalent lens system. In addition, because of the broad spectrum, lenses will induce chromatic aberrations that cause different wavelengths to focus at different locations. Mirrors are inherently achromatic and provide the same focus regardless of wavelength. Chromatic aberration present at the fiber optic cable 116 can cause portions of spectrum not to be coupled as well into the fiber optic cable 116 creating more loss in portions of the spectrum where more chromatic aberration is present. However, a large drawback to mirrors is that mirrors will generally require more space than lens-based systems.

Figure 3A:
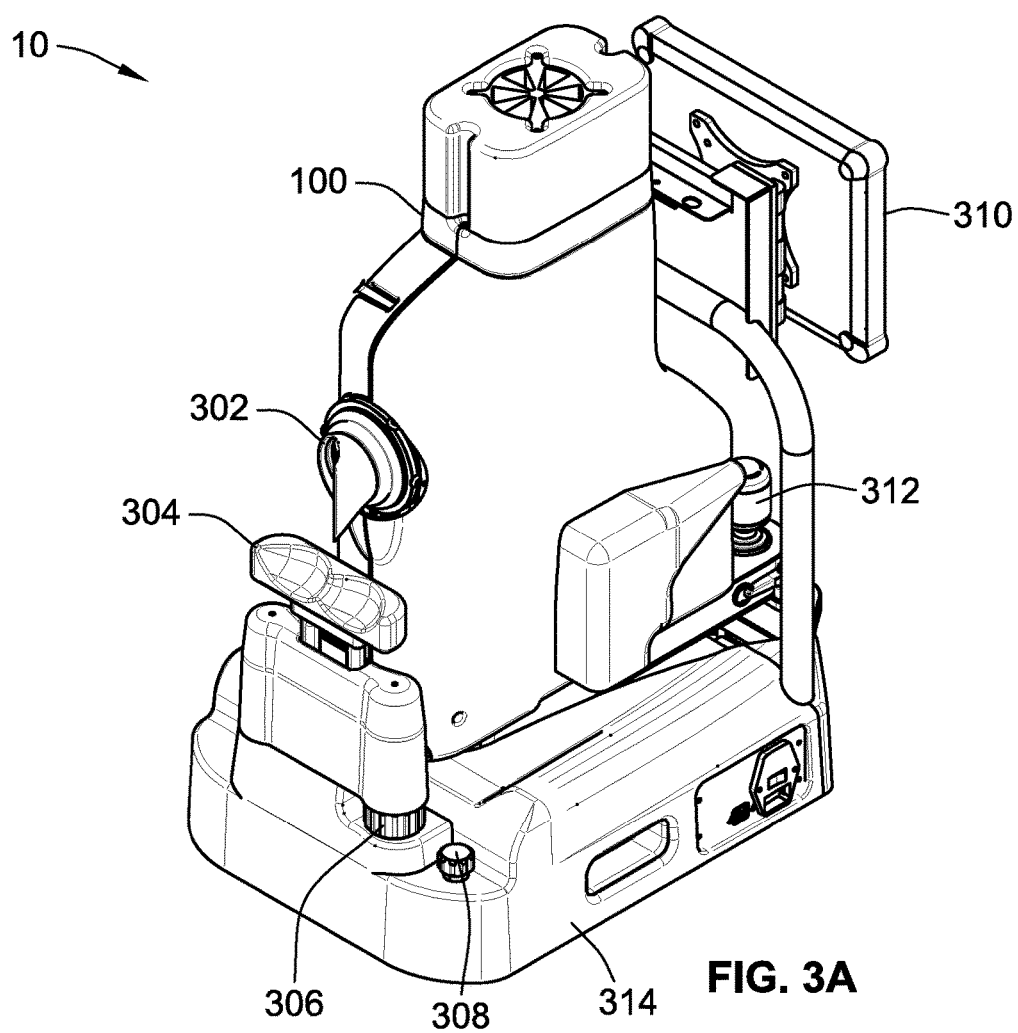
FIG. 3A is a patient-side perspective view of a reflectometry instrument as used on a patient according to aspects of the present disclosure.
Figure 3B:
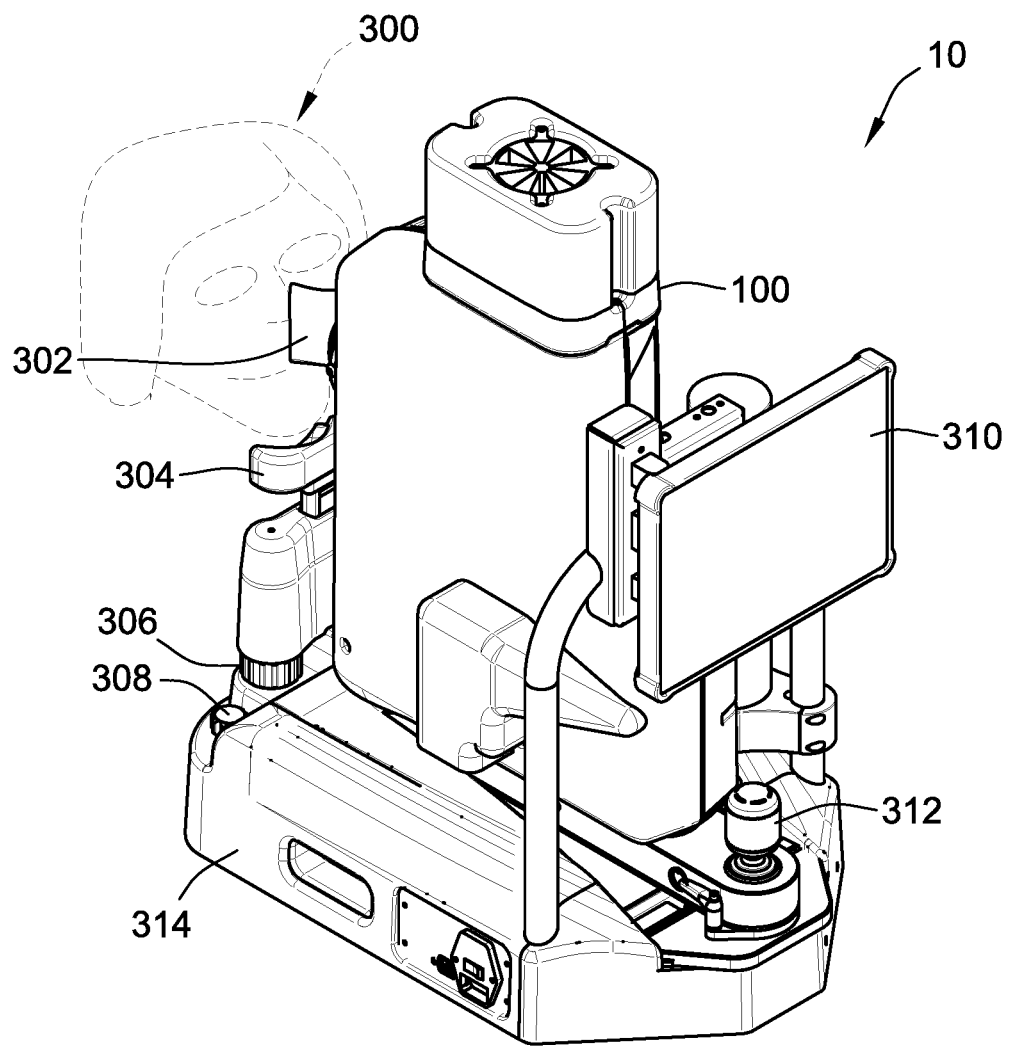
FIG. 3B is a technician-side perspective view of a reflectometry instrument as used on a patient according to aspects of the present disclosure.

Referring now to FIGS. 3A and 3B, one physical embodiment of the reflectometry instrument 10 is illustrated relative to the patient 300. The patient 300 is positioned at one side of the reflectometry instrument 10 (e.g., patient side). The reflectometry instrument 10 includes an eyepiece 302 that is shaped to conform to the patient's eye socket around the eye. The eyepiece 302 prevents or at least limits external light from entering the reflectometry instrument 10 or the patient's eye while the patient's eye is positioned against the eyepiece 302. The eyepiece 302, in part, allows for analysis of the patient's eye to occur without dilating the pupil. In addition, the eyepiece 302 allows, in part, for an examination using the instrument 10 to be performed in a lit environment, such as a lit office environment (e.g., office lights on).

Below the eyepiece 302 is a chin rest 304 to provide support for the patient's head during the examination. The chin rest 304 can include an adjuster 306 to control the position (e.g., height) of the chin rest 304 relative to the eyepiece 302 to maximize patient comfort.

On the same side as the eyepiece 302 is an adjuster 308. As discussed above, the translation systems 208 and 216 are configured to translate the lenses 110c and 114b, respectively, to adjust illumination and reflection to accommodate for correction of the patient's diopter. The movement of the lenses 110c and 114b by the translation systems 208 and 216 is controlled by software instructions responsive to patient inputs. These patient inputs can be inputted using the adjuster 308. For example, the patient 300 can rotate the adjuster 308 clockwise and/or counterclockwise to cause the reflectometry instrument 10 to translate the lenses 110c and 114b. Upon the patient 300 adjusting for their diopter, the adjuster 308 can be locked to prevent accidental inputs from changing the configuration of the reflectometry instrument 10 during an examination. For example, once the patient has adjusted the lenses 110c and 114b prior to the analysis, the patient control over the lenses 110c and 114b is then locked out to avoid accidental changes during a procedure.

On the opposite side of the reflectometry instrument 10 from the eyepiece 302 is a display 310. The display 310 provides information to the technician before, during, and after an examination. For example, the display 310 can provide information regarding the position of the reflectometry instrument 10 relative to the patient 300, as discussed in detail below. The display 310 also allows the operator (e.g., technician, optometrist, ophthalmologist, etc.) of the reflectometry instrument 10 to view in real time the analysis performed by the reflectometry instrument 10 and the corresponding results. In some aspects, the display 310 can be a touch screen display that displays software controls for the instrument 10 and serves as an interface for the technician to use while controlling the instrument 10.

To align the reflectometry instrument 10 with the patient's eye, the reflectometry instrument 10 also includes a joystick 312. The joystick 312 allows the technician to alter the position of the reflectometry instrument 10 in three-dimensional space to align the reflectometry instrument 10 with the patient's eye. In some aspects, the joystick 312 can be configured to control one or more devices (e.g., motors, servos, actuators, or the like, not shown) in the base 314 of the reflectometry instrument 10 to control the position of the upper housing 100 relative to the patient 300. Alternatively, the joystick 312 can be mechanically coupled to one or more axes of movement to manually move the housing 100 under the power of the operator. The movements of the instrument 10 in the three dimensions (up/down, left/right, and back/forth) can be accomplished with the base 314 of the instrument 10, which is mounted on a table or other fixed foundation. The eyepiece 302 and the chin rest 304 provide the patient 300 with a comfortable fit, while also fixing the location of the patient's head (and retina) relative to the upper housing 100 after being adjusted by the joystick 312.

In some aspects, the reflectometry instrument 10 can also include a manual scale (not shown) (e.g., measured in diopters) on the outside of the instrument 10 that corresponds to movement of the lenses 110c and 114b. In some alternative aspects, the information provided by such a scale can instead be provided on the display 310 (e.g., digital representation of a scale). The adjuster 308 can be manipulated to move the lenses 110c and 114b to locations that correspond to the patient's spectacle prescription, which information can be provided by the manual or digital scales.

In some aspects, the reflectometry instrument 10 can include one or more external calibration targets, such as the calibration target 316, as discussed in further detail below with respect to FIG. 5.

Referring to FIG. 4, in some embodiments, the reflectometry instrument 10 can include an imaging system 400. The imaging system 400 is used for imaging the pupil of the eye. More specifically, the imaging system 400 allows the reflectometry instrument 10 to be aligned to the patient's eye, thus maximizing the detection beam 204 reflected from the retina of the patient's eye onto the fiber optic cable 116.

The imaging system 400 includes a light source 402. As shown, the light source 402 can be located on the exterior of the housing 100 of the reflectometry instrument 10 but within the eyepiece 302. Alternatively, the light source 402 can be located within the housing 100. The light source 402 provides light that illuminates the patient's eye 220 for imaging the pupil 224. The light source 402 can be an array of LEDs. Alternatively, the light source 402 can be other sources of light without departing from the present disclosure. Light from the light source 402 reflects off the patient's eye and passes through the window 128, similar to the detection beam 204 described above.

Unlike the illumination beam 202 and the detection beam 204, the light from the light source 402 passes through the dichroic fold mirror 126. To pass through the dichroic fold mirror 126, as opposed to reflecting like the illumination beam 202 and detection beam 204, the light from the light source 402 can be a different wavelength of light. For example, the light from the light source 402 can be IR light, and the dichroic fold mirror 126 can be configured to transmit IR light while reflecting the light of the illumination beam 202 and the detection beam 204.

After passing through the dichroic fold mirror 126, the reflected light reflects off a mirror 404 and is directed to a camera 406. The camera 406 provides a live image of the eye 220 based on the received light from the light source 402. The live image can be presented on the display 310 discussed above. The live image allows an operator of the reflectometry instrument 10 to align the instrument 10 prior to illuminating the patient's eye with the illumination beam 202 for maximizing the resulting detection beam 204. In some aspects, the display 310 can present a reticle (e.g., crosshairs and the like) overlaid on the live image of the human eye for the operator to align the human eye with the illumination beam 202. As discussed above, the operator of the instrument 10 can move the joystick 312 based on the live image from the camera 406 to position the upper housing 100 relative to the patient's eye 220. The joystick 312 can similarly be locked so that accidental contact with the joystick 312 does not affect the position of the upper housing 100 during an examination.

Although shown and described specifically with respect to the elements of the reflectometry instrument 10 discussed above, in some aspects, the imaging system 400 can be used within any other reflectometry instrument, such as a conventional instrument that does not include the elements of the separation system 106 discussed herein. For conventional reflectometry instruments, alignment with the patient's eye is still required. Thus, the imaging system 400 can be included within such instruments to improve the alignment with the patient's eye and increase the quality of the resulting detection beam.

Figure 5:
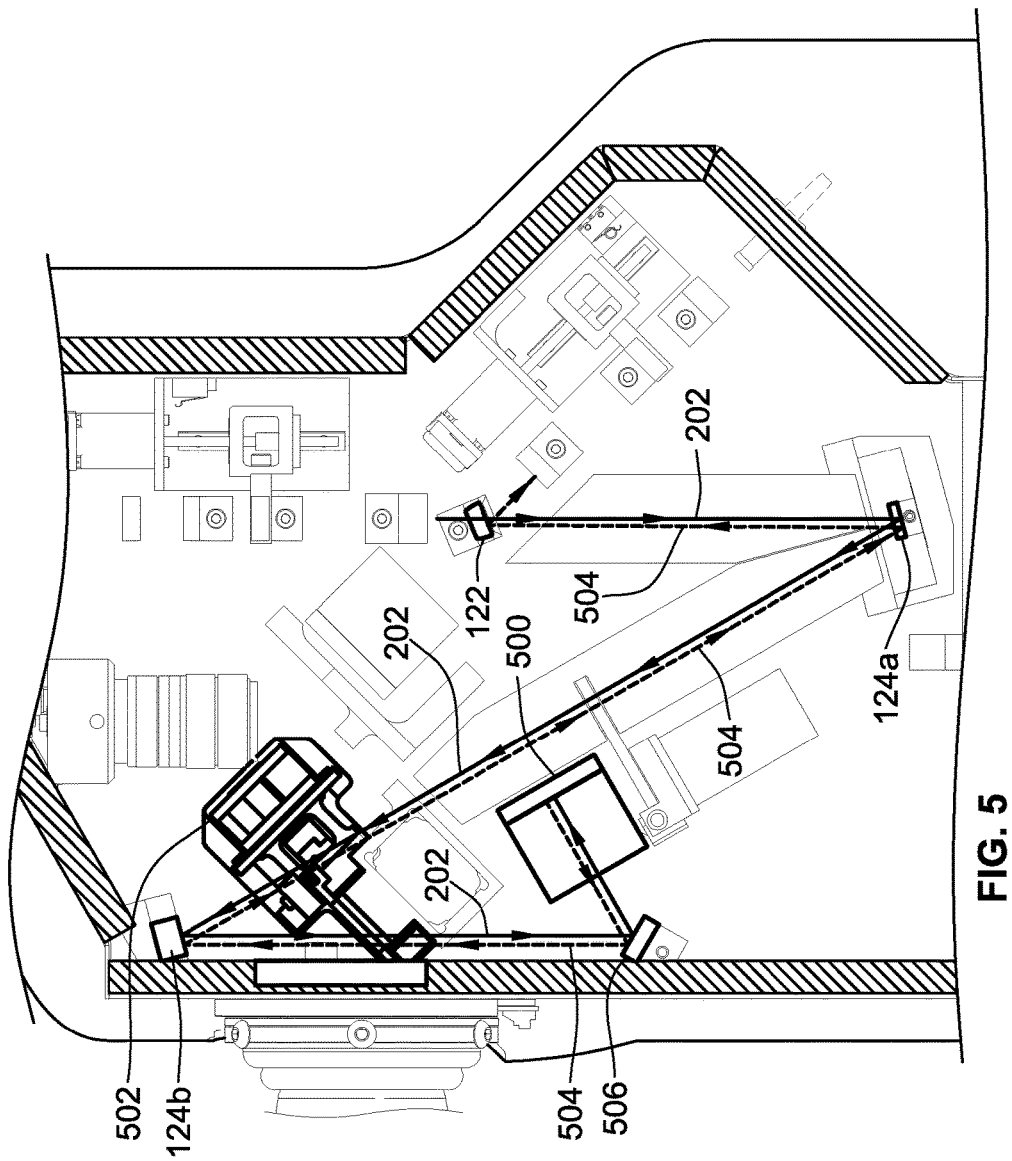
FIG. 5 is a schematic of a calibration target within a reflectometry instrument according to aspects of the present disclosure.

Referring to FIG. 5, in some aspects, the reflectometry instrument 10 can include a calibration target 500. The calibration target 500 is a model eye with known characteristics that can be used to calibrate the reflectometry instrument 10. For example, the calibration target 500 can provide a known reflection reflectance standard for the reflectometry instrument 10. In some aspects, the calibration target 500 can be a black calibration target used to determine stray light within the system for generating a baseline that is subtracted out of the detection beam path. The calibration target 500 is configured to be illuminated by the illumination beam 202 in place of the patient's eye. In response to the illumination beam 202, the calibration target 500 produces a reflected beam 502 having specific characteristics. The reflected beam 502 is then directed to the spectrometer 118 by the separation system 106 and the detection system 104, similar to the detection beam 204. The spectrometer 118 then analyzes the reflected beam 502 to calibrate the reflectometry instrument 10.

To optionally direct the illumination beam 202 to the patient's eye or the calibration target 500, the dichroic fold mirror 126 can be movable. For example, the dichroic fold mirror 126 can be configured to reflect the illumination beam 202 toward the patient's eye in a first position and reflect or allow the illumination beam 202 to pass by toward the calibration target 500 in a second position. The dichroic fold mirror 126 can selectively flip, rotate, or otherwise move between the two positions depending on whether the patient's eye or the calibration target 500 is the intended target of the illumination beam 202. To move the dichroic fold mirror 126 between the two positions, the dichroic fold mirror 126 can be connected to a device 504 (e.g., motor, servo, actuator, or the like) that can manually move the dichroic fold mirror 126 in response to the desired function.

The illumination beam 202, once past the dichroic fold mirror 126, either can image the calibration target 500 directly or can reflect off one or more mirrors, such as the mirror 506. The resulting reflected beam 502 then reflects off the mirror 506 in the direction of the detection system 104. The presence of the mirrors, such as the mirror 506, can depend on the location of the calibration target 500.

Having the calibration target 500 within the reflectometry instrument 10 provides for a more controlled environment for calibration and the convenience of merely altering the arrangement of the dichroic fold mirror 126. Further, although only one calibration target 500 within the instrument 10 is shown and described (e.g., black calibration target), in some aspects the reflectometry instrument 10 can include multiple calibration targets, such as two targets, three targets, etc. In some aspects, the reflectometry instrument 10 can include two calibration targets, such as a black calibration target and a white calibration target.

In addition to, or in the alternative, the instrument 10 can include one or more external calibration targets, such as the external calibration target 316 shown in FIG. 3B. The external calibration targets can include the calibration target types not within the housing 100 of the instrument 10. For example, the external calibration target 316 can be a white calibration target when the calibration target 500 within the housing 100 is a black calibration target. The external calibration target 316 is configured to be secured to the housing 100 at the eyepiece 302 to be imaged similar to a patient's eye. That is, the external calibration target 316 can be removed from a storage position (as shown in FIG. 3B) and secured to the housing 100 at the eyepiece 302. An illumination beam and detection beam can then be generated, as described above, but with the external calibration target 316 the imaged object rather than a patient's eye. Once calibration using the external calibration target 316 is completed, the external calibration target 316 can be removed from the eyepiece 302 and stored on the instrument 10.

Although shown and described specifically with respect to the elements of the reflectometry instrument 10 discussed above, in some aspects, the calibration target 500 can be used within any other reflectometry instrument, such as a conventional instrument that does not include the elements of the separation system 106 discussed herein. For conventional reflectometry instruments, calibration is still required. Thus, the calibration target can be included within such instruments to improve the ease with which the instrument is calibrated.

Figure 6:
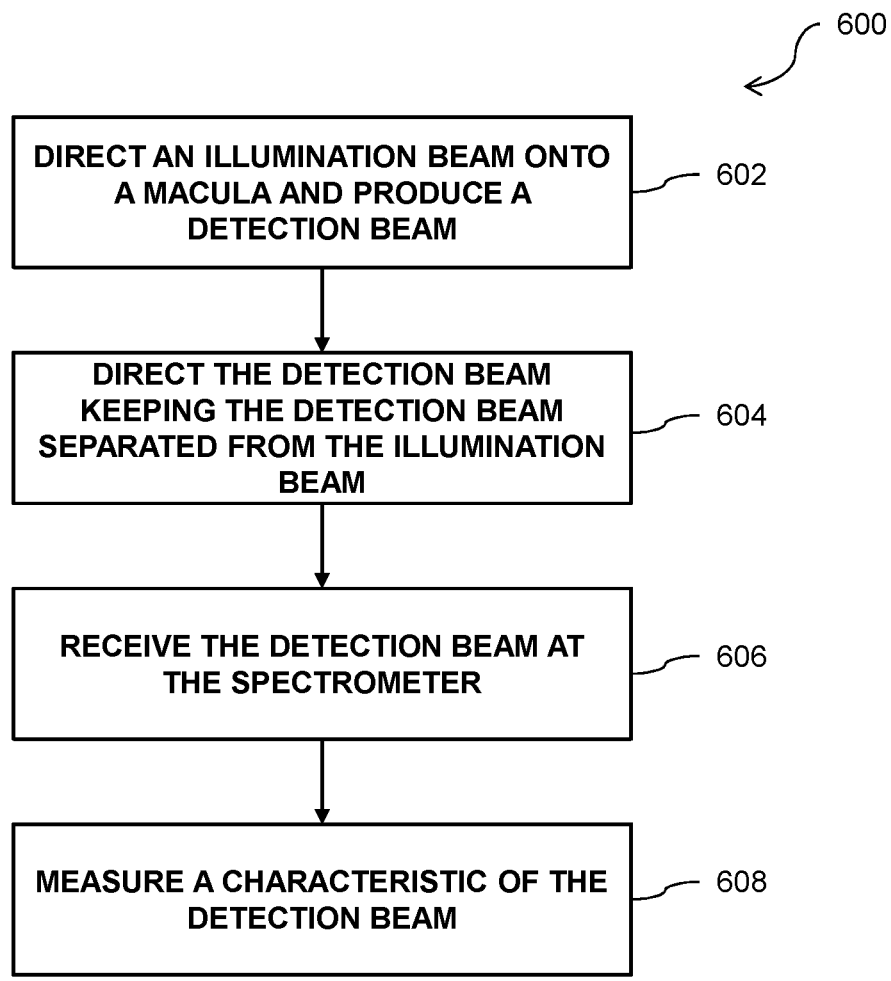
FIG. 6 is a flow chart of a process of determining the amount of macular pigment in a macula of a human eye according to aspects of the present disclosure.

Referring to FIG. 6, a flow chart of a process 600 of determining the amount of macular pigment in a macula of a human eye is shown according to aspects of the present disclosure. The method can be performed by using a reflectometry instrument according to the present disclosure, such as the instrument 10.

At step 602, an illumination beam from an illumination source is directed onto the macula of a patient's eye via a series of mirrors. The illumination source and the series of mirrors produce an illumination beam as described above that illuminates about a 1-degree area of the macula of the patient's eye. The illumination beam is generated to produce a detection beam that reflects from the macula.

At step 604, the detection beam is directed from the macula and to a spectrometer via the series of mirrors. The detection beam reflects off the series of mirrors offset from the illumination beam such that the detection beam and the illumination beam remain separated. In some aspects, the mirrors can be configured so that the illumination beam and the detection remain parallel relative to each other at the mirrors. For example, the illumination beam reflected from a mirror can be parallel to the detection beam incident at the mirror. Similarly, the illumination beam incident at a mirror can be parallel with the detection reflected from the mirror.

At step 606, the detection beam is received at an instrument that is configured to analyze the detection beam, such as a spectrometer. In some aspects, the detection beam can be reflected toward the instrument, without the illumination beam, based on the detection beam reflecting off of a D-shaped mirror and with the illumination beam being out of alignment with the D-shaped mirror.

At step 608, the spectrometer analyzes the detection beam to generate data characterizing the detection beam. In some aspects, the detection beam is analyzed at 2048 data points, corresponding to the 2048 different wavelengths measured at every programmed integration time point. For example, at an integration time of 100 ms and a reading time of 10 seconds, a total of 1000 readings will be taken at all of the 2048 wavelengths measured.

This generated data can then be analyzed to determine the macular pigment, melanin, lens optical density, and other characteristics of the patient's eye. In some aspects, the data can be processed according to one or more algorithms to result in a macular pigment optical density (MPOD) score, among other results. Information on the macular pigment of the patient's eye can subsequently be used to determine, for example, the amount of macular degeneration the patient is suffering from and/or the amount of lutein and/or zeaxanthin within the macula.

In some embodiments, the one or more algorithms can include, or access information on, non-naturally occurring objects present in the patient's eye, such as intraocular lenses or any other surgically implanted object. The information can be any specification of the object that can affect the illumination beam and/or detection beam and, therefore, affect the generated data. For example, the information can include information on an intraocular lens that the patient has, such as reflectivity information, and how the reflectivity information can effect measurements of the patient's eye and the resulting generated data. The reflectometry instrument (e.g., instrument 10 or spectrometer 118) can contain memory that stores the information on the objects in one or more databases. The memory can be the same memory or different memory that stores the one or more algorithms.

For example, in cases where the patient has an intraocular lens, the one or more algorithms can account for the particular intraocular lens using the information stored in the database. That is, the reflectometry instrument can account for how the intraocular lens affects the illumination beam and/or detection beam when analyzing the generated data to provide an accurate analysis of the patient's eye, correcting or reducing effects of the intraocular lens. As a specific example, the specification for optical absorption of the intraocular lens can be substituted into the reference absorption spectra to replace the patient's naturally age sensitive lens's signature. Thus, despite non-naturally occurring objects being present in the eye, such as intraocular lenses, the analysis of the generated data by the reflectometry instrument can account for and correct or reduce any effect the objects have on the analysis of the eye.

It should be also noted that the techniques described above with respect to macular pigment also apply to the determination of characteristics of the lens within the eye. Accordingly, the present invention may also be useful for determining the early stages of aging of the human lens or first signs of cataract formation, without needing to dilate the patient's eyes.

Each of these embodiments and obvious variations thereof is contemplated as falling within the spirit and scope of the claimed invention, which is set forth in the following claims.

The invention claimed is:

1. A reflectometry instrument to measure macular pigment of a macula of a human eye, comprising:
    a housing including an illumination system, a detection system, and a beam dump, the illumination system configured to generate an illumination beam and direct the illumination beam to the macula, a detection beam being generated as a portion of the illumination beam reflected by the macula, the detection system configured to receive and measure the detection beam to determine an amount of the macular pigment in the macula, and the beam dump being in optical alignment with an optical input of the detection system for absorbing stray light within the reflectometry instrument; and
    an eyepiece connected to the housing and being configured to interface with the human eye to prevent ambient light from entering the housing,
    wherein the beam dump and the eyepiece allow the reflectometry instrument to measure the macular pigment of the macula in a lit environment.

2. The reflectometry instrument of claim 1, wherein the reflectometry instrument is configured to obtain and process at least 1000 images of the macula per second for measuring the amount of the macular pigment.

3. The reflectometry instrument of claim 1, further comprising one or more lenses, one or more mirrors, or a combination thereof within the housing for directing the illumination beam to the macula and directing the detection beam from the macula.

4. The reflectometry instrument of claim 3, wherein the illumination beam and the detection beam are kept separated between the one or more lenses, the one or more mirrors, or a combination.

5. The reflectometry instrument of claim 1, wherein the illumination system includes a first mirror for reflecting the illumination beam toward the macula and for reflecting the detection beam from the macula.

6. The reflectometry instrument of claim 5, wherein the illumination beam and the detection beam reflect off the first mirror offset from each other.

7. The reflectometry instrument of claim 5, wherein an incident ray of the illumination beam and a reflected ray of the detection beam at the first mirror are parallel.

8. The reflectometry instrument of claim 5, further comprising:
    a series of mirrors for reflecting the illumination beam toward the macula and for reflecting the detection beam from the macula,
    wherein the first mirror is included within the series of mirrors.

9. The reflectometry instrument of claim 8, wherein the illumination beam and the detection beam reflect off each mirror of the series of mirrors offset from each other.

10. The reflectometry instrument of claim 8, further comprising:
    a calibration target for modeling an eye and having a known reflection reflectance standard,
    wherein the series of mirrors includes a moveable mirror for selectively imaging the human eye or the calibration target in place of the human eye for calibrating the reflectometry instrument.

11. The reflectometry instrument of claim 8, wherein the series of mirrors includes a D-shaped mirror, the D-shaped mirror being arranged relative to the illumination beam to allow the illumination beam to pass by the D-shaped mirror and being arranged relative to the detection beam to reflect the detection beam.

12. The reflectometry instrument of claim 1, wherein the detection system comprises a spectrometer for measuring the detection beam.

13. The reflectometry instrument of claim 1, wherein the housing further includes a window allowing light from the human eye to pass therethrough, the reflectometry instrument further comprising:
    an imaging system for providing a live image of the human eye prior to illuminating the human eye with the illumination beam.

14. The reflectometry instrument of claim 13, wherein the imaging system comprises a camera for generating the live image in response to receiving the light from the human eye.

15. The reflectometry instrument of claim 14, further comprising:
   a light source for generating the light received from the human eye, light from the light source illuminating and reflecting off the human eye to generate the light received from the human eye, and subsequently passing through the window.

16. The reflectometry instrument of claim 15, wherein the light source is an array of light emitting diodes.

17. The reflectometry instrument of claim 13, wherein the imaging system is configured to relate an alignment of the reflectometry instrument to the human eye based on a reticle represented within the live image.

\* \* \* \* \*